United States Patent [19]

Lu

[11] Patent Number: 4,697,454

[45] Date of Patent: Oct. 6, 1987

[54] COMBINED HYDROMETER FOR TESTING THE BATTERY AND RADIATOR FLUID

[76] Inventor: Shwu-Ching Lu, P.O. Box 32-223, Taipei, Taiwan

[21] Appl. No.: 801,967

[22] Filed: Nov. 26, 1985

[51] Int. Cl.[4] .............................................. G01N 9/16
[52] U.S. Cl. ...................................... 73/440; 73/441; 73/454
[58] Field of Search ................. 73/440, 441, 442, 443, 73/444, 451, 454

[56] References Cited

U.S. PATENT DOCUMENTS

| | | | |
|---|---|---|---|
| 3,691,847 | 9/1972 | Wallskog | 73/454 |
| 3,722,292 | 3/1973 | Pietramale | 73/454 |
| 3,908,467 | 9/1975 | Schwen et al. | 73/454 |
| 4,353,253 | 10/1982 | Callahan | 73/454 |

FOREIGN PATENT DOCUMENTS 543515  7/1957  Canada ................... 73/454

Primary Examiner—John Chapman
Attorney, Agent, or Firm—Wenderoth, Lind & Ponack

[57] ABSTRACT

A combined hydrometer for measuring the specific gravity of a radiator fluid and a battery fluid including a fluid chamber having a transparent front window, a substantially horizontal axis in the chamber, an upper battery fluid scale having readings corresponding to the specific gravity of a battery fluid and a lower calibrated scale having readings corresponding to the freezing temperature of a radiator fluid. An indicator float and a second float are mounted eccentrically in the fluid chamber for pivotal movement about the axis, the indicator float having a relatively smaller specific gravity than the second float and being mounted on the axis between the second float and the front window. The indicator float normally rests with a tip end therof facing a lowermost point on the radiator fluid scale and the second float normally rests with a tip end thereof facing a lowermost point on the battery fluid scale. A projection extending from the indicator float towards the second float carries the second float along with the indicator float when the indicator float is angularly deflected beyond the resting position of the second float. The combined hydrometer permits measurement of the freezing temperature of a radiator fluid when the fluid chamber is filled with a radiator fluid and also allows measurement of the specific gravity of a battery fluid when the fluid chamber is filled with a battery fluid.

4 Claims, 5 Drawing Figures

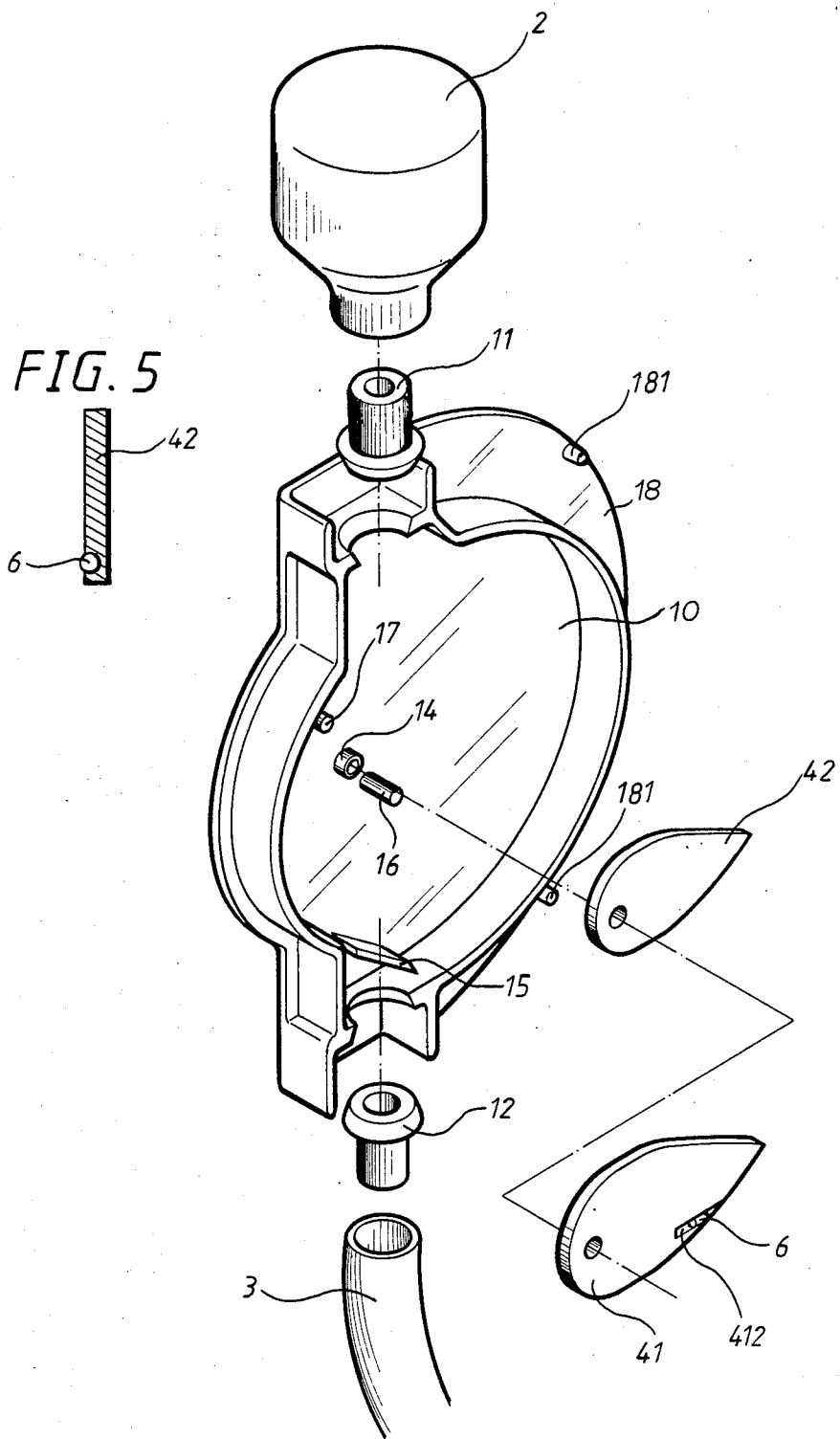

COMBINED HYDROMETER FOR TESTING THE BATTERY AND RADIATOR FLUID

BACKGROUND AND SUMMARY OF THE INVENTION

This invention relates to a combined hydrometer for testing a battery fluid and a radiator fluid, particularly for measuring the specific gravity of the fluid or the freeze temperature thereof.

In the current hydrometer for measuring the specific gravity of the battery fluid or the radiator fluid, there are the types such as shown in U.S. Pat. Nos. 3,691,847 and 3,722,292.

Since the range of the specific gravity of a battery fluid and a radiator fluid is different, two kinds of hydrometers have to be used, that is, for an automobile, there must be two different hydrometers, but that requirement has caused inconvenience to the user as well as additional cost from the economic point of view.

In the conventional hydrometer, the weight block in the float is directly and substantially fixed in a hole without the possibility of any adjustment later on.

Although some conventional hydrometers do have their weight blocks adjustably mounted, their structures are all deemed rather complicated.

Moreover, since the flexible intake tube of the conventional hydrometer is usually mounted to the body thereof, there arises inconveniences in carrying or shipping, and packing the device. Of course, the intake tube may be disassembled from the body, but it is susceptible to being misplaced occasionally.

In view of the aforesaid disadvantages of the conventional hydrometer, it is an object of the present invention to provide a combined hydrometer including two floats pivotally mounted in parallel on the same shaft for measuring the specific gravity of a battery fluid and a radiator fluid.

It is another object of the present invention to provide a combined hydrometer, in which the weight blocks on the floats can easily be mounted for adjusting the precise specific gravity if necessary.

It is still another object of the present invention to provide a combined hydrometer, of which the intake hose may, when not in use, be mounted in a channel furnished along the edge of the hydrometer body for convenience in carrying, packing, and shipping thereof.

BRIEF DESCRIPTION OF THE DRAWING

FIG. 4 is a perspective view of the device according to the present invention in a disassembled state.
FIG. 5 is a sectional view of the float in the present invention.

DETAILED DESCRIPTION

Figure 1:
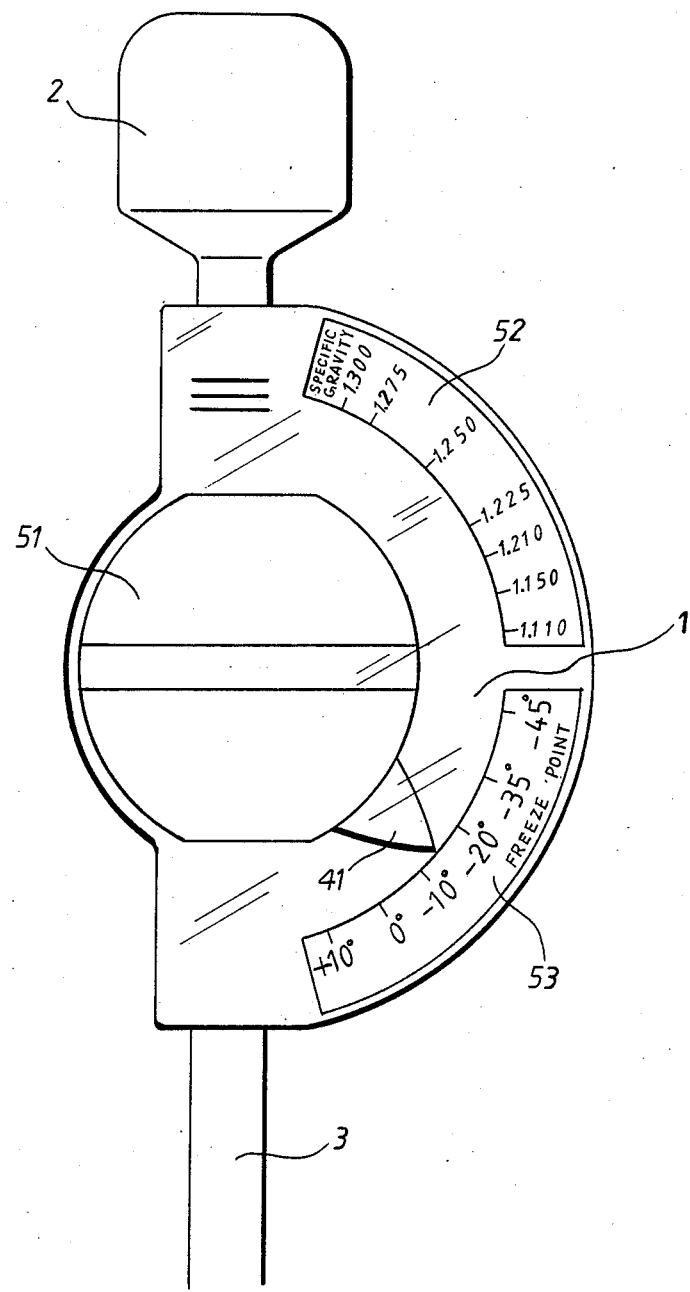
FIG. 1 is a front view of a combined hydrometer according to the present invention.

In testing the antifreeze fluid in a radiator, the value of the specific gravity of the antifreeze fluid has to be obtained first. Currently, the temperature at which the fluid in the radiator of an automobile freezes ranges from +10° F. to −45° F. (or −12° C. to −43° C.), which corresponds to a value of specific gravity in the range of from 1.0454 to 1.0801. When testing the battery fluid, the main point is to measure the specific gravity between the sulfuric acid and the water so as to find out whether the normal specific gravity is maintained or not, that is, the specific gravity is usually in the range of from 1.100 to 1.300. In general, when the specific gravity reading is between 1.100 to 1.210, the battery will need to be recharged, when the reading is between 1.210 to 1.260, it indicates that the battery is in fair condition and when the reading is in the range of from 1.260 to 1.300, the battery is in good condition.

According to the aforesaid description, it is indicated that the highest specific gravity (1.0801) of water in a radiator is below the lowest specific gravity of water in a battery, a feature which the present invention makes use of.

Referring to FIGS. 1 to 4, there is shown a fluid chamber 10 according to the present invention, which includes a transparent window 1 of a semi-circular shape and made of a transparent plastic material. The top end and bottom end of chamber 10 are provided with pipe joints 11 and 12, respectively.

The pipe joint 11 is fitted with a means for drawing fluid into chamber 10, such as a flexible manually operated air bulb 2, while the pipe joint 12 is fitted with a detachable intake tube 3. On the front side of the chamber 10 provided with the window 1, there is attached a label 51 containing operating instructions. Along one edge of the front side, there are provided a plurality of calibrated scales such as two specific gravity scales 52 and 53 on a front surface portion of the window 1, i.e. an upper scale 52 for indicating the specific gravity of the battery fluid and a lower scale 53 for indicating the freezing point of the radiator water. An indicator float 41 is pivotally mounted in the chamber 10 such that a tip thereof can be seen through the window 1 during measuring.

Figure 2:
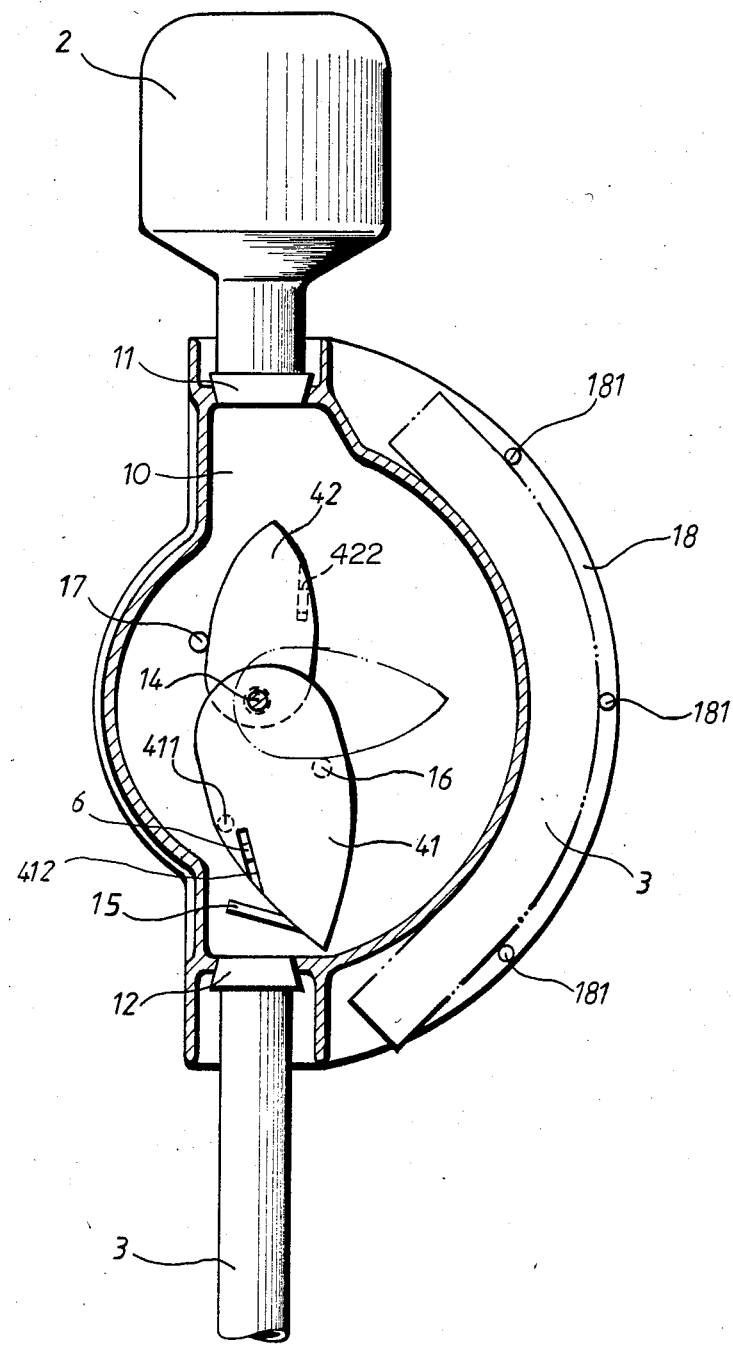
FIG. 2 is a front sectional view of FIG. 1.
Figure 3:
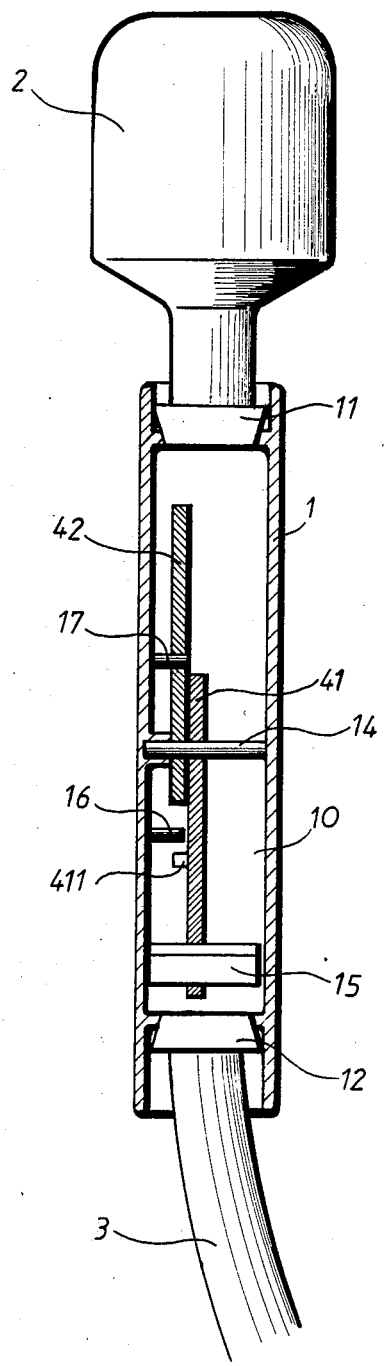
FIG. 3 is a side sectional view of FIG. 1.

As shown in FIGS. 2 and 4, a substantially horizontal axis 14 is provided in the chamber 10. A plurality of floats are eccentrically mounted in the chamber for pivotal movement about the axis 14, the floats comprising the aforesaid indicator float 41 and a second float 42. The indicator float 41 is dimensioned such that a front surface thereof lying in a plane perpendicular to the axis 14 is larger than a similar surface of the float 42, whereby the float 42 is hidden from view by the indicator float 41 when the float 42 is directly behind the float 41. The tip of indicator float 41 is normally pointing downwards and rests against a stop block 15 provided in the chamber 10 with the tip end of the float 41 aligned with the lowermost reading on the lower scale 53. The other float 42 is normally positioned horizontally with a tip end thereof at a resting point facing towards the lowermost reading of the specific gravity scale 52 of the battery fluid and rests against a limiting post 16 provided in the chamber 10. A limiting post 17 provided in the chamber 10 limits the extent of upper movement of float 42. On the rear side of the indicator float 41, there is mounted carrying means, such as a pushing stud or projection 411 extending towards the second float 42 for carrying the second float 42 upon movement of the indicator float 41 across the resting point of the second float 42. Whenever the indicator float 41 is pushed upwards as a result of a heavier specific gravity of the battery fluid, the pushing stud 411 will engage the float 42 and push it upwards simultaneously. In that case, the float 42 will be hidden behind the indicator float 41.

In order to accurately test the specific gravities of the radiator fluid and the battery fluid, the floats 41 and 42 must have different standard specific gravities, respectively, the float 41 having a relatively smaller specific gravity than the float 42. Referring to FIG. 2, both floats 41 and 42 include elongated slots 412 and 422, respectively on their front sides, in which respective weights 6 made of metal are mounted. The position of the weight 6 in each of the slots 412 and 422 may be varied so as to adjust the specific gravity of each of the floats 41 and 42, if necessary. Of course, the magnitude of each weight 6 is set to a standard weight and each weight 6 is embedded at a suitable position in the respective slot to meet the requirements of the floats 41 and 42 before shipment of the hydrometer from a factory. In a situation in which any one of the weights or the floats are not made accurately, minor calibration of the particular float can be made by adjusting the position of the weight 6 in the slot.

The floats 41 and 42 are made of plastic material which allows the weights 6 to be easily embedded in the elongated slots 412 and 422 by pressing in on the weights. The weights 6 in the slots 412 and 422 can be positioned by using a slender rod to push the weights 6 to the desired position therein. As shown in FIG. 5, the weight 6 can be cylindrical and slidably fitted in a semicylindrical slot open on one side of the float 42.

The total specific gravity of the indicator float 41 is adjusted by positioning the weight 6 such that the indicator float 41 is adaptable to test the specific gravity of the radiator fluid, but the indicator float 41 can not be used for measuring the specific gravity of the battery fluid. Both the specific gravity scale 53 of the radiator fluid and the specific gravity scale 52 of the battery fluid have the same length, but the difference between the upper and lower limits of the specific gravity of the radiator fluid is $1.0801 - 1.0454 = 0.0347$, while the difference between the upper and lower limits of the specific gravity of the battery fluid is $1.300 - 1.100 = 0.200$. As such, the second float 42 is used for increasing the weight of float 41, i.e., the float 41 will push the float 42 upon moving upwards to an extent necessary to meet the requirements for measuring the specific gravity of the battery fluid.

Upon compressing and expanding the air bulb 2 to draw radiator fluid, via the intake hose 3, into the chamber 10, the float 41 will be floated to angularly deflect about the axis 14 and pivot upwardly with the tip end thereof within the range between the uppermost and lowermost limits of the readings calibrated in freeze temperature degrees on the radiator fluid scale 53 so as to indicate the temperature at which the radiator fluid will freeze, while the float 42 remains in its normal position without moving. When the chamber 10 is filled with battery fluid having a higher specific gravity than the radiator fluid, the float 41 will angularly deflect about axis 14 beyond the uppermost reading of the specific gravity scale of the radiator fluid, and the float 41 will engage the float 42 with its pushing stud 411 to pivot the float 42 until reaching a position at the reading which indicates the correct specific gravity of the battery fluid.

Referring to FIGS. 2 and 4, there is shown a channel formed by two parallel flange portions 18 extending along one side of the chamber 10 for mounting the intake hose 3 therein. Further, one side of the channel is provided with several studs 181 at regular spaced intervals extending between the outer edges of the flanges 18. The studs prevent the intake hose 3 from falling out of the channel, whereby the length of the entire hydrometer can be reduced during periods when it is not in use or when it is packed for shipping.

I claim:

1. A combined hydrometer for mesuring the specific gravity of a radiator fluid and a battery fluid comprising a fluid chamber having a transparent front window, a substantially horizontal axis in said chamber, a plurality of calibrated scales on a front surface portion of said window, a plurality of floats each of which is mounted eccentrically in said fluid chamber for pivotal movement about said axis, said scales including a lower scale having readings calibrated for the freezing temperature of a radiator fluid and an upper scale having readings corresponding to specific gravity values of a battery fluid, said floats including an indicator float and a second float, said indicator float having a relatively smaller specific gravity than said second float and being mounted on said axis between said second float and said front window, said indicator float normally resting with an end thereof towards a lowermost point of said radiator fluid scale, said second float normally resting with an end thereof towards a lowermost point of said battery fluid scale, carrying means associated with said indicator float and said second float for carrying said second float along with said indicator float when said indicator float is angularly deflected about said axis beyond the resting position of said second float, whereby when said fluid chamber is filled with radiator antifreeze fluid said indicator float will be floated thereby to angularly deflect about said axis to indicate a reading within the radiator fluid scale so as to measure the specific gravity or the freeze temperature of said radiator antifreeze fluid, and when said fluid chamber is filled with battery fluid said indicator float will be floated thereby to angularly deflect about said axis into the battery fluid scale whereupon said carrying means effects pivotal movement of said second float therewith to indicate a reading within the battery fluid scale so as to measure the specific gravity of said battery fluid.

2. A combined hydrometer as claimed in claim 1, wherein said indicator float has a specific gravity smaller than that corresponding to the lower-most calibrated value of said radiator fluid scale so as to be able to angularly deflect and indicate a reading within said radiator fluid scale upon immersion in a normal radiator antifreeze fluid and said second float has a specific gravity larger than that of a normal battery fluid, the average specific gravity of the second float when carried by said indicator float being relatively smaller than but approximately equal to that of the lowermost calibrated value of said battery fluid scale so as to be able together said indicator float to angularly deflect and indicate a reading within said battery fluid scale upon immersion in a normal battery fluid.

3. A combined hydrometer as claimed in claim 1, wherein said carrying means comprises at least one projection extending from said indicator float towards said second float whereby said indicator float engages said second float and carries said second float together therewith upon angular deflection of said indicator float, said fluid chamber including stop block means for supporting said indicator float in a rest position with a tip end thereof aligned with the lowermost point of the radiator fluid scale when fluid is not present in said chamber, and limiting post means disposed in said fluid chamber for supporting said second float in a rest position when fluid is not present in said chamber.

4. A combined hydrometer for measuring the specific gravity of a radiator fluid and a battery fluid comprising a fluid chamber having a axis in said chamber, a plurality oftransparent front window, a horizontalsubstantially calibrated scales on a front surface portion of said window, a plurality of floats each of which is mounted eccentrically in said chamber for pivotal movement about said axis, said scales comprising a lower scale with readings calibrated in freeze temperature degrees for radiator fluid and an upper scale with readings directly showing specific gravity values for battery fluid, said floats comprising an indicator float and a second float, said indicator float having a relatively larger front dimension surface and a relatively smaller specific gravity than said second float and said indicator float being pivotally mounted between said second float and said front window with a tip end of said indicator float normally resting towards the lowermost point of said radiator fluid scale, said second float having a tip end thereof normally resting towards the lowermost point of said battery fluid scale suuch that said second float can be hidden behind said indicator float, said indicator float having carrying means for carrying said second float upon movement of said tip end of said indicator float across the resting point of said second float, whereupon said chamber being filled with radiator antifreeze fluid causes said indicator float to angularly deflect about said axis and register with a reading within the radiator fluid scale so as to indicate the specific gravity or the freeze temperature of said antifreeze fluid, and whereupon said chamber being filled with battery fluid causes said indicator float to angularly deflect about said axis into the battery fluid scale to carry said second float together therewith an to register with a reading within the range of the battery fluid scale so as to indicate the specific gravity of said battery fluid.

* * * * *